United States Patent [19]

Lagace

[11] 4,427,018

[45] Jan. 24, 1984

[54] DENTAL FLOSS HOLDER

[76] Inventor: Yves Lagace, 1re Avenue Nord, Weedon, Quebec, Canada, J0B 3J0

[21] Appl. No.: 365,490

[22] Filed: Apr. 5, 1982

[51] Int. Cl.³ ............................................... A61C 15/00
[52] U.S. Cl. ........................................ 132/91; 433/141
[58] Field of Search .................... 132/91; 433/216, 161

[56]  References Cited

U.S. PATENT DOCUMENTS

| 1,815,408 | 7/1931 | Jordan | 132/91 |
| 2,517,806 | 8/1950 | Streiler | 132/91 |
| 2,828,754 | 4/1958 | Stewart | 132/91 |

Primary Examiner—Robert Peshock
Attorney, Agent, or Firm—Swabey, Mitchell, Houle, Marcoux & Sher

[57] ABSTRACT

A dental floss holder for holding a length of dental floss under tension comprises an elongated handle and a bifurcated head at one end of the handle, the bifurcated head having a pair of opposed spaced-apart resilient arms defining a gap between the terminal ends thereof. Each terminal end of the arms is provided with an outwardly extending flange and a floss receiving groove, the groove at one terminal end being aligned with the groove at the other terminal end such that a length of the floss bridges the gap. Each groove has a bottom defined by a rounded convex surface for frictionless engagement with the floss to permit the floss to freely slide thereon as the arms inwardly yield towards one another upon the application of tension to the floss. The flange of each arm includes a pair of opposed flange portions defining, as an extension of the groove, a guide opening therebetween for guiding the floss and maintaining same positioned on the bottom surface at each terminal end. The dental floss holder of the invention further includes anchoring means for releasably securing the floss with the length thereof extending between the terminal ends of the arms being maintained under tension by the outward resilient force exerted by the arms.

5 Claims, 9 Drawing Figures

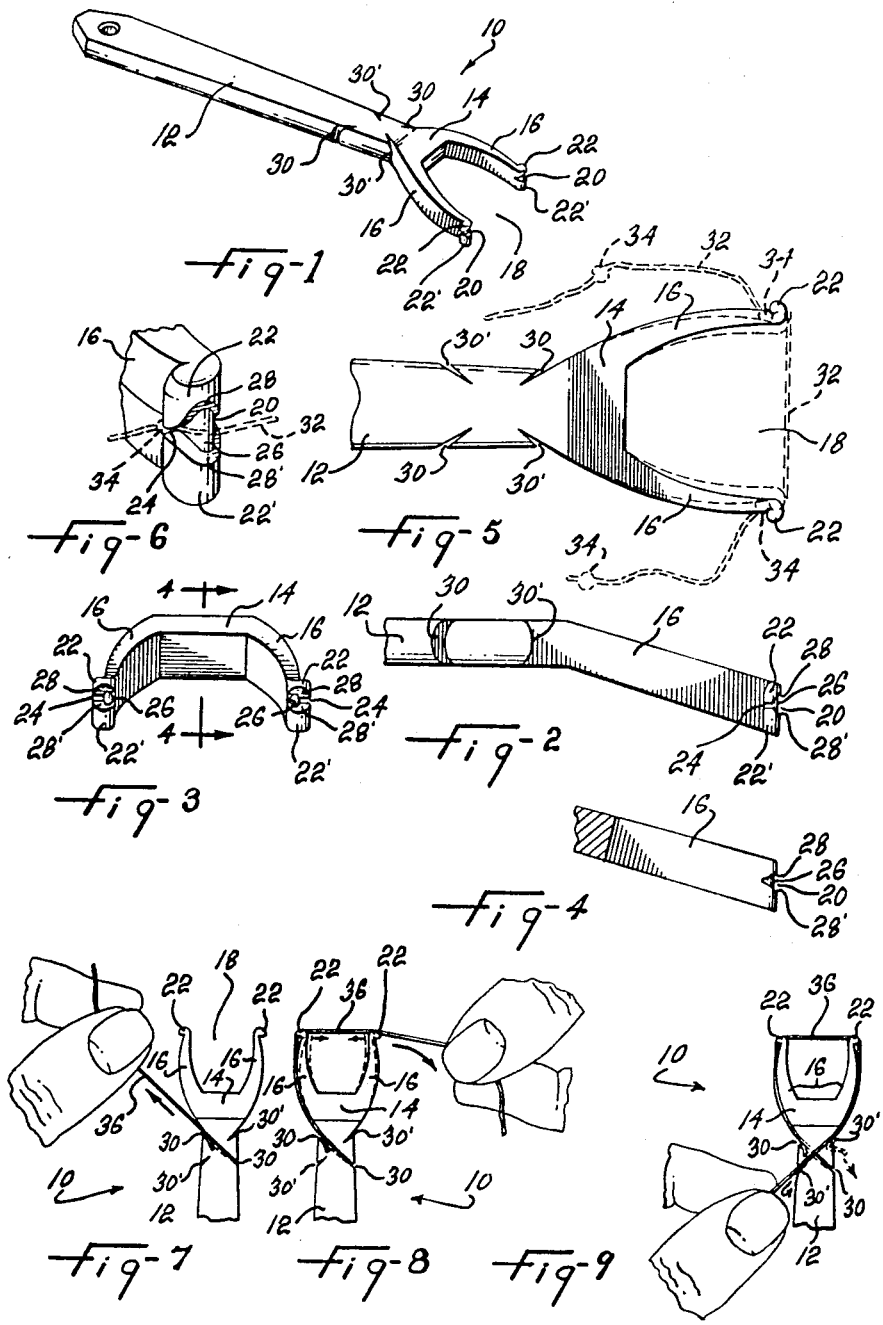

DENTAL FLOSS HOLDER

BACKGROUND OF THE INVENTION

The present invention relates to a device for holding dental floss for the purpose of facilitating the removal with same of foreign matter lodged between adjacent teeth in the mouth. The invention is more particularly concerned with a dental floss holder of the type wherein a length of dental floss can be held under tension.

Various dental floss holders have already been described, for instance, in U.S. Pat. Nos. 1,815,408 and 2,354,454. The dental floss holder of U.S. Pat. No. 1,815,408 is adapted to hold under tension a special type of dental floss having knots or enlargements at predetermined lengths therealong and, to this end, it comprises a pair of opposed spaced-apart floss anchoring arms which are slitted at their terminal ends to receive the floss, each slit intersecting a recess formed in the outer side of each arm and having a size and shape to accommodate a knot of the floss. Since the arms are resilient and the length of floss between two successive knots is slightly smaller than the distance between the terminal ends of the arms, by first compressing the arms so as to yield towards each other and inserting the length of floss between two successive knots through the slits at the terminal ends of the arms and then releasing the arms, the knots will engage the recesses in the arms and remain anchored therein, thus resulting in the tensioning of the length of floss therebetween. This dental floss holder, however, has a drawback in that the floss often gets dripped between the walls of the slits and thereby prevents the arms from springing back toward their initial positions, and it is thus often necessary to pull the arms away from each other so as to ensure that the knots are securely seated in the recesses formed therein. Also, since dental floss is generally a multi-filament thread, some filaments do get split apart when the floss is inserted in the slits owing to the right frictional engagement with the walls of the slits, causing the floss to fray.

The dental floss holder proposed in U.S. Pat. No. 2,354,454, on the other hand, is adapted to hold under tension a conventional floss, that is, one having a substantially uniform cross-section throughout its entire length. The holder similarly has a pair of opposed spaced-apart resilient arms but these are provided with aligned floss receiving notches at their terminal ends, instead of slits. Outwardly extending cleats are arranged on the outer sides of the arms remote from the terminal ends thereof for the purpose of anchoring the end portions of a length of such a floss which has been inserted in the notches at the terminal ends of the arms. Laterally projecting lugs are also provided on the outer sides of the arms between their terminal ends and the cleats thereon. Since the portions of floss between the cleats and the terminal ends of the arms extend in straight lines along the outer side edges of the arms once the floss has been engaged with the notches and the cleats, by snapping these portions of floss across the lugs the floss will be stretched and placed under tension. Thus, tensioning of the floss is achieved only after it has been engaged with the notches and the cleats and the arrangement does not enable one to adjust the tension to different values. A further drawback resides in that the floss has a tendency to get wedged in the notches and thereby to prevent the arms from inwardly yielding towards each other during movement of the floss into engagement with the lugs, which as a consequence hinders the tensioning of the floss.

SUMMARY OF THE INVENTION

It is therefore an object of the present invention to overcome the above-mentioned drawbacks and to provide a dental floss holder which prevents the floss from wedging at the ends of the arms holding same and thus allows the arms to move towards or away from each other without hindrance when tension is applied to the floss, regardless of whether the floss used is of the special type described previously or of the conventional type.

In accordance with the invention, there is provided a dental floss holder for holding a length of dental floss under tension, which comprises an elongated handle and a bifurcated head at one end of the handle, the bifurcated head having a pair of opposed spaced-apart resilient arms defining a gap between the terminal ends thereof. Each terminal end of the arms is provided with an outwardly extending flange and a floss receiving groove, the groove at one terminal end being aligned with the groove at the other terminal end such that a length of the floss bridges the gap. Each groove has a bottom defined by a rounded convex surface for frictionless engagement with the floss to permit the floss to freely slide thereon as the arms inwardly yield towards one another upon the application of tension to the floss. The flange of each arm includes a pair of opposed flange portions defining, as an extension of the groove, a guide opening therebetween for guiding the floss and maintaining same positioned on the bottom surface at each terminal end. The dental floss holder of the invention further includes anchoring means for releasably securing the floss with the length thereof extending between the terminal ends of the arms being maintained under tension by the outward resilient force exerted by the arms.

The provision of floss receiving grooves at the terminal ends of the arms, which each have a rounded convex bottom surface for frictionless engagement with the floss, ensure that the floss will not hang up in the grooves but rather will freely slide on the bottom surfaces when tension is applied to the floss. The floss guide openings which are also provided at the terminal ends assist in maintaining the floss positioned on the bottom surfaces of the grooves so as to prevent the floss from slipping off the ends of the arms.

According to a preferred embodiment, where the dental floss used has at least two enlargements formed thereon and spaced one from another by a length smaller than the gap, the guide opening is smaller than the enlargements such that each pair of flange portions at each terminal end serve as respective pair of abutment shoulder portions to thereby define the aforesaid anchoring means. Thus, by anchoring both enlargements against the pairs of abutment shoulder portions adjacent their associated guide openings with the length of floss between the two enlargements extending through the guide openings and bridging the gap, the length of floss will be securely held under tension by the arms.

According to another preferred embodiment, where use is made of a dental floss having a substantially uniform cross-section throughout its entire length, the anchoring means comprise first and second pairs of diagonally aligned floss retaining notches, a respective one of the notches of each pair being disposed on a respective one of opposite sides of the handle. The notches of the first pair cooperate to anchor one end portion of the floss while those of the second pair cooperate to anchor the opposite end portion of the floss.

The dental floss holder of the invention preferably includes both the above forms of floss anchoring means so as to provide a versatile implement which can accommodate both the above-mentioned types of dental floss.

BRIEF DESCRIPTION OF THE DRAWINGS

Further advantages and features of the invention will become apparent from the following detailed description of a preferred embodiment thereof as illustrated by way of example in the accompanying drawings, wherein:

FIG. 1 is an oblique top view of a dental floss holder according to a preferred embodiment of the invention;

FIG. 2 is a fragmentary side view of the dental floss holder illustrated in FIG. 1;

FIG. 3 is an end view of the dental floss holder showing the head thereof;

FIG. 4 is a sectional view taken along line 4—4 of FIG. 3;

FIG. 5 is a fragmentary top view of the dental floss holder as seen holding under tension the knotted type of dental floss, with the dental floss represented in broken line;

FIG. 6 is a fragmentary enlarged perspective view of one arm of the dental floss holder shown in FIG. 5; and FIGS. 7-9 are fragmentary front elevation views showing how the conventional type of dental floss may be attached to the holder so as to be securely held under tension.

DESCRIPTION OF PREFERRED EMBODIMENTS

Referring first to FIGS. 1-4, there is illustrated a dental floss holder generally designated by reference numeral 10 and comprising an elongated handle 12 and a bifurcated head 14 at one end of the handle. The head 14 has a pair of opposed inwardly curved resilient arms 16 which are spaced-apart to define a gap 18 between the terminal ends thereof. The arms 16 lie in a plane which is inclined at an angle of about 40° relative to the longitudinal axis of the handle. The terminal ends of the arms are flanged and provided with aligned outwardly flaring floss receiving grooves 20 which each extend through the flange at the end of each arm 16 to define a pair of opposed flange portions 22 and 22' and a floss guide opening 24 therebetween. As shown, the flange portions 22 and 22' project laterally outwardly from the sides of the arms 16.

The grooves 20 each have a rounded convex bottom surface 26 with an apex and opposite spaced-apart sidewalls 28 and 28' which diverge outwardly in the region of the apex. Each groove 20 is also enlarged in the region of the apex and gradually narrows on either side thereof, as best shown in FIGS. 2 and 4.

In order to anchor the end portions of a conventional dental floss when using such a floss, two pairs of diagonally aligned notches 30 and 30' are provided in the handle 12 adjacent the head 14, the notches 30 and 30' of the respective pairs being formed in the sides of the handle with the diagonal defined by one pair of notches crossing that define by the other pair of notches. The notches 30 cooperate to securely anchor one end portion of the floss while the notches 30' cooperate to securely anchor the opposite end portion of the floss.

As shown in FIGS. 5 and 6, when using the special type of dental floss 32 represented in broken line and having knots or enlargements 34 at predetermined lengths therealong, the guide opening 24 provided at the end of each arm 16 is dimensioned such as to prevent a knot 34 from passing therethrough and to thereby arrest the knot in abutting engagement against the flange portions 22 and 22' which thus serve as abutment shoulders. Therefore, to attach such a floss to the holder 10, one simply has to anchor one knot 34 at the end of one arm 16 against the flange portions 22 and 22' thereof adjacent the guide opening 24 with the floss 32 extending through the opening 24 and over the bottom surface 26 of the groove 20, and then to insert the floss in the groove 20 at the end of the other arm 16 to thereby bridge the gap 18. Thereafter, the floss 32 is pulled so as to inwardly flex the arm 16 to which the knot 34 is anchored and thus pass the next knot 34 through the groove 20 at the latter end and over the edge of the flange 22,22' to snap same thereunder.

Since the length of floss 32 between two successive knots 34 is slightly smaller than the gap 18, the arms 16 will yield toward each other to occupy the positions shown in broken line in FIG. 5, the length of floss bridging the gap 18 being then maintained under tension by the outward resilient force exerted by the arms 16. It should be noted that the guide openings 24 also maintain the floss positioned on the bottom surfaces 26 of the grooves 20, as best shown in FIG. 6. Furthermore, the same attachment procedure may be followed when using a similar type of dental floss which is usually available at a dentist's office and which has only two knots or enlargements 34 with a finger-loop end portion extending from one of the knots.

Turning now to FIGS. 7-9, in order to attach a conventional dental floss 36 which has a substantially uniform cross-section throughout its entire length, one end portion of the floss is first wedged in the notch 30 on the left-hand side face of the handle 12 adjacent the head 14, then carried diagonally across the back face of the handle and wedged in the other notch 30 on the right-hand side face of the handle remote from the head and thereafter carried again diagonally across the front face of the handle, as shown in FIG. 7. As a result, the floss 36 has its one end portion securely anchored in the notches 30 and, since the notches taper inwardly, the latter will be tightly gripped between the walls of the notches and will not be liable to slip loose.

Then, the floss 36 is carried upwardly along the outer side of the left arm 16 through the guide opening 24 and into the groove 20 at the end of the arm, and then across the gap 18 and into the groove 20 at the end of the right arm 16, as shown in FIG. 8. As the floss is carried downwardly along the outer side of the right arm 16 and enters through the guide opening 24 at its end, it is pulled to tension the length thereof between the ends of the arms 16, causing the arms to yield toward each other and to occupy the positions shown in broken line in FIG. 8. The finger gripped end portion of the floss under tension is finally wrapped diagonally about the handle 12 such that it is wedged first in the notch 30' on the left-hand side face of the handle 12 remote from the head and then in the other notch 30' on the right-hand side face of the handle adjacent the head, so as to securely anchor same as shown in FIG. 9. The floss 36 has thus its end portions secured to the handle 12 with the length thereof extending between the ends of the arms 16 being held under tension by the outward resilient force exerted by the arms. Since the floss 36 freely slides on the rounded convex bottom surface 26 of the groove 20 at the end of each arm 16 during the tensioning of the floss, it is apparent that the tension applied to the floss may be readily adjusted.

Furthermore, it should be noted that since the flange 22,22' at the end of each arm 16 projects laterally outwardly, the teeth being cleaned have access to the area closely adjacent the inner sides of the arms 16 where the floss is more rigid and thus provides better cleaning.

As the dental floss holder 10 illustrated can accommodate both types of dental floss 32 and 36 shown respectively in FIGS. 5–6 and 7–9, it also constitutes a versatile implement.

I claim:

1. A dental floss holder adapted to receive a dental floss having at least two enlargements formed thereon and spaced one from another by a predetermined length, for holding said length of floss under tension, said holder comprising an elongated handle and a bifurcated head at one end of said handle, said bifurcated head having a pair of opposed spaced-apart resilient arms defining a gap between terminal ends thereof with said gap having a width greater than said predetermined length, each terminal end of said arms being provided with an outwardly extending flange and a floss receiving groove, the groove at one terminal end being aligned with the groove at the other terminal end and each said groove having a bottom defined by a rounded convex surface for frictionless engagement with floss positionable therein, the flange of each arm including a pair of opposed flange portions defining, as an extension of the groove, a guide opening therebetween for guiding floss and maintaining same positioned on said bottom surface at each said terminal end, said guide opening being smaller than said enlargements such that each said pair of flange portions at each said terminal end serve as respective pair of abutment shoulder portions to thereby define first anchoring means for releasably securing said floss such that said length thereof when bridging said gap is maintained under tension by outward resilient force exerted by said arms, whereby when a respective one of said two enlargements is anchored against a respective one of said pairs of abutment shoulder portions adjacent a respective one of said guide openings with the length of floss between said two enlargements extending through said guide openings and bridging said gap, said length of floss is securely held under tension by said arms.

2. A dental floss holder as claimed in claim 1, wherein each said groove is defined by opposite sidewalls and said bottom surface and wherein said bottom surface includes an apex and said sidewalls are spaced apart and diverge outwardly in the region of said apex.

3. A dental floss holder as claimed in claim 1, further adapted to receive a dental floss having a substantially uniform cross-section throughout its entire length and further including second anchoring means comprising first and second pairs of diagonally aligned floss retaining notches, a respective one of said notches of each said pair being disposed on a respective one of opposite sides of said handle, the notches of the first pair cooperating to anchor one end portion of said floss of uniform cross-section and those of the second pair cooperating to anchor the opposite end portion of said floss.

4. A dental floss holder as claimed in claim 1, wherein said arms lie in a plane which is angularly inclined relative to the longitudinal axis of said handle.

5. A dental floss holder as claimed in claim 1, wherein said arms are inwardly curved whereby to aid in the inward flexing thereof upon the application of tension to said floss.

* * * * *